United States Patent [19]
Binder et al.

[11] Patent Number: 5,285,681
[45] Date of Patent: Feb. 15, 1994

[54] ON-LINE PELLET DURABILITY TESTER

[75] Inventors: Stephen F. Binder, Washington; Lawrence F. Reutzel, St. Louis; David J. Rothermel, New Haven, all of Mo.

[73] Assignee: Purina Mills, Inc., St. Louis, Mo.

[21] Appl. No.: 759,102

[22] Filed: Sep. 6, 1991

Related U.S. Application Data

[63] Continuation of Ser. No. 630,918, Dec. 20, 1990, abandoned.

[51] Int. Cl.$^5$ .............................................. G01N 3/00
[52] U.S. Cl. ................................................................ 73/78
[58] Field of Search ................... 73/7, 12, 78, 821, 866

[56] References Cited

U.S. PATENT DOCUMENTS

| | | | |
|---|---|---|---|
| 3,698,647 | 10/1972 | Nye | 241/24 |
| 3,766,776 | 10/1973 | Williams | 73/12 |
| 3,791,222 | 2/1974 | Goodhart et al. | 73/866 |
| 4,210,290 | 7/1980 | Anderson et al. | 241/34 |
| 4,449,670 | 5/1984 | Tloczynski et al. | 241/35 |
| 4,633,712 | 1/1987 | Scieszka | 73/866 |
| 4,703,647 | 11/1987 | Eckhoff et al. | 73/78 |
| 4,761,990 | 8/1988 | Baillie | 73/866 |
| 4,856,716 | 8/1989 | Burstedt | 241/30 |
| 4,856,909 | 8/1989 | Mehta et al. | 73/866 |
| 5,021,940 | 6/1991 | Cox et al. | 241/34 |

FOREIGN PATENT DOCUMENTS

| | | |
|---|---|---|
| 0040406 | 11/1981 | European Pat. Off. . |
| 0095168 | 11/1983 | European Pat. Off. . |
| 3312942 | 10/1984 | Fed. Rep. of Germany . |
| 2466338 | 4/1981 | France . |
| 55-90629 | 7/1980 | Japan . |
| 8502491 | 9/1985 | Netherlands . |
| 8102238 | 8/1981 | PCT Int'l Appl. . |
| 2136271 | 5/1975 | U.S.S.R. . |
| 513298 | 5/1976 | U.S.S.R. . |
| 680700 | 8/1979 | U.S.S.R. . |
| 2181559A | 4/1987 | United Kingdom . |

OTHER PUBLICATIONS

Feed Manufacturing Technology, AFMA (1976) pp. 528–529.
"The Progressive Animal Feed Production and Its Fundamentals–Part 3: Pelleting in Practice" by R. Schultz at pp. 6–31 of *Advances in Feed Technology*, No. 3/Spring 1990, and pp. 27–28, Section 2.17.

*Primary Examiner*—Robert Raevis
*Attorney, Agent, or Firm*—Whyte Hirschboeck Dudek

[57] ABSTRACT

The durability of extruded, uncured animal feed pellets is measured by disintegrating the pellets in a test chamber by means of a rotating blade powered by an electric motor. During the test, the rotating blade is maintained at or near a constant rate of rotation and the time over which an increase of power is necessary to drive the blade at constant rotation is sensed to determine the durability of the pellets.

15 Claims, 3 Drawing Sheets

ON-LINE PELLET DURABILITY TESTER

This is a continuation of co-pending application Ser. No. 07/630,918 filed on Dec. 20, 1990 now abandoned.

BACKGROUND OF THE INVENTION

1. Field of the Invention

This invention relates to pellet durability testing. In one aspect, the invention relates to a device for testing the durability of pellets while in another aspect, the invention relates to a method of testing the durability of pellets, particularly uncured pellets.

2. Description of the Prior Art

Pellets, here defined as an agglomeration (however formed, e.g. by pellet mill, extruder, etc.) of individual ingredients (typically ground ingredients), or a mixture of such ingredients or their equivalents, are a convenient form for a variety of products, e.g. animal feeds, pharmaceuticals, dietary supplements, water treatments, etc. Pellets offer ease of handling from manufacture through consumption, and allow considerable freedom in functional design, e.g. nutritional composition, size, shape, and the like.

Because pellets are usually subjected to a considerable amount of jostling from the time of their manufacture to the time of their ultimate consumption or use, and because many end uses require or have a preference for pellets with good structural integrity, such as many dry animal feed products, durability is an important physical property of the pellet. Durability, i.e. the resistance of a pellet to significant deterioration over time, can be measured by a variety of different tests, the K-State Pellet Quality Test for animal feed products being representative. This test is described in detail at pages 528-9 of Section 6 of Appendix F to *Feed Manufacturing Technology*, published by the Feed Production Council of the American Feed Manufacturers Association (1976). While this and similar tests provide a useful durability measure for a pellet, here an animal feed pellet, the principal disadvantage of these tests are that they are performed on cured pellets, i.e. pellets that have been collected, dried, cooled and/or screened. By the time these steps have been completed, a production run, often measured in tons of product, has been completed and if the pellet durability is poor, then the pellets of that production run must either be reprocessed or disposed as off-specification product. This is particularly true of extruded pellets where considerable time can elapse between pellet formation, usually at elevated temperature, pressure and water content (an uncured state), and the measurement of durability of a hard, dry pellet (finished product or cured state).

As such, the determination of pellet durability is most desirably made shortly after the pellet is formed such that if the durability of the pellet is found to be poor, then one or more process parameters, such as increasing or decreasing the amount of binder, steam, compaction pressure, etc., can be adjusted immediately to bring pellet durability into compliance with a desired specification. Such an on-line testing device should be able to perform the test quickly, efficiently and repeatedly over the course of a production run. In addition, the testing device should be readily adaptable to existing pellet manufacturing equipment and procedures.

SUMMARY OF THE INVENTION

According to this invention, pellet durability is measured by a process comprising the steps of: A. collecting a sample of the pellets into a test chamber, B. disintegrating the sample of pellets within the test chamber by mechanical means, and C. measuring by sensing means the disintegration of the sample of pellets within the test chamber by the mechanical means.

Step (C) of this process can be performed by any one of a number of different techniques such as measuring the time required to disintegrate a portion or all of the pellets, or measuring the energy or power requirements of the mechanical means to disintegrate a portion or all of the pellets, etc.

This process can be performed by using a pellet durability tester which comprises:
1. a test chamber equipped with
   a. a first port through which a sample of pellets can enter the chamber, and
   b. mechanical means for disintegrating the pellets into pellet fines and pellet fragments,
2. drive means for operating the mechanical means, and
3. sensing means for measuring the disintegration of the pellets by the mechanical means.

The measurement of the pellet disintegration, whatever its nature and units, can be used without modification as the pellet durability measure, or it can be converted to an existing durability standard, such as the K-State Pellet Quality Test.

The process and pellet durability tester of this invention can provide quick, efficient and repeated durability measurements of pellets within moments of their manufacture. This in turn allows changes to be made to one or more of the manufacturing parameters while the process is still in progress.

DETAILED DESCRIPTION OF THE INVENTION

Like numerals are employed to designate like parts throughout the drawings. Various items of equipment, such as electrical connections, fittings, and the like, have been omitted from the drawings so as to simplify the description of the pellet durability tester. However, those skilled in the art will realize that such conventional equipment can be employed as desired.

Figure 1:
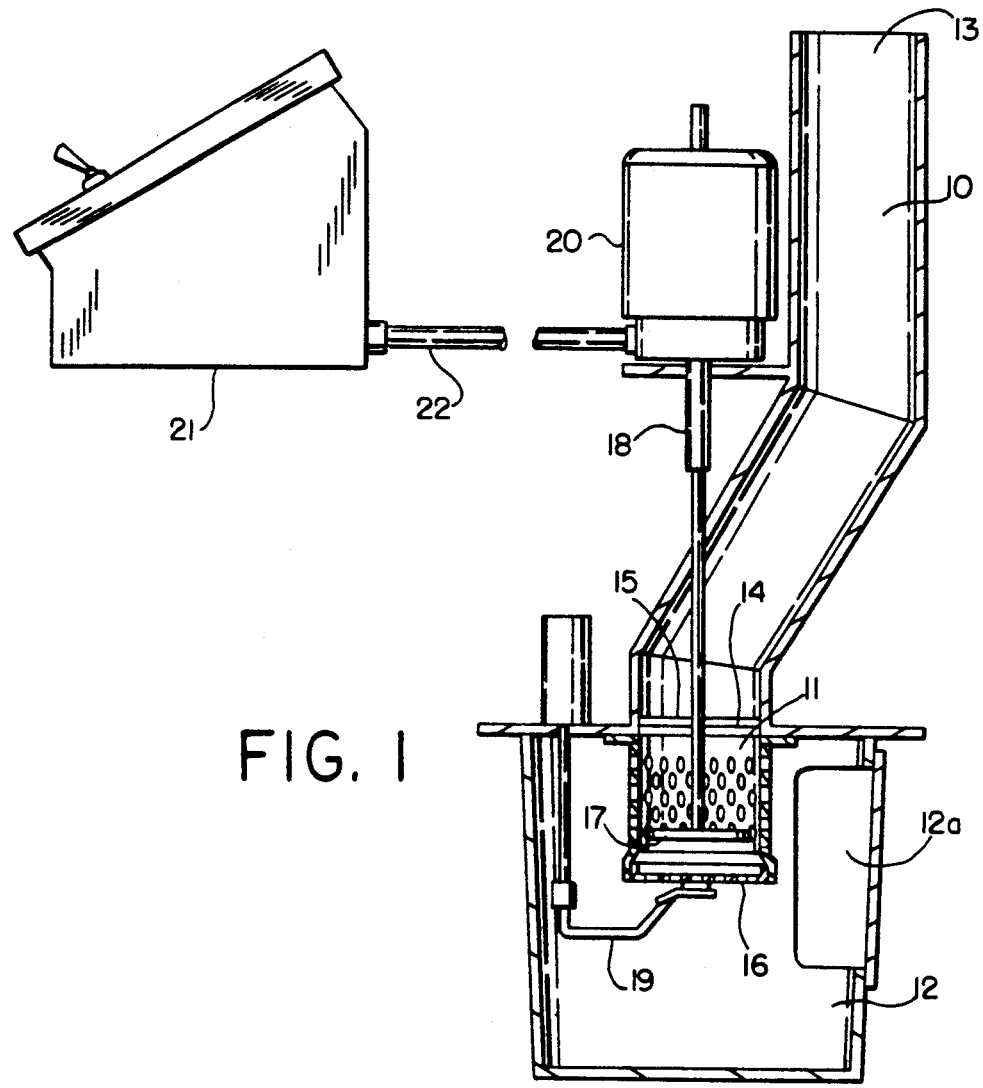
FIG. 1 is a side view and cross-section of one embodiment of a pellet durability tester suitable for performing the process of this invention.

In FIG. 1, one embodiment of an on-line pellet durability tester is shown, and it comprises an optional sample inlet chamber 10 attached to a test chamber 11 enclosed within a housing 12. Door 12a on housing 12 allows access to test chamber 11. The inlet chamber 10 has an entrance port 13 and an exit port 14, the latter of which is in open communication with test chamber 11. Port 14 is equipped with a gate 15 that when in the closed position, will retain a sample of pellets within inlet chamber 10 and when in the open position, will discharge the pellets from inlet chamber 10 into test chamber 11. Gate 15 can be positioned at any point along the length of inlet chamber 10 that is convenient to the operation of the pellet durability tester. Entrance port 13 can also be equipped with a gate (not shown) if desired to regulate the intake of pellets from a pellet mill or any other source to inlet chamber 10.

Figure 2:
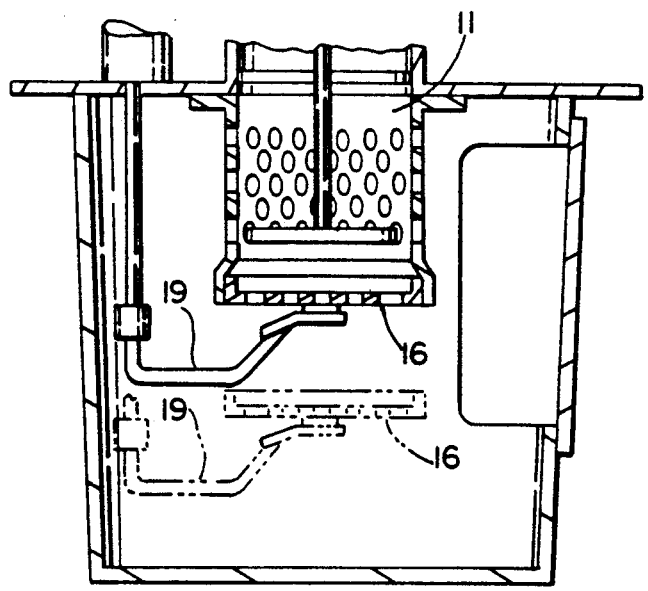
FIG. 2 is a side view and cross-section of the test chamber of the pellet durability tester of FIG. 1.

Test chamber 11 is equipped with a floorgate 16 and a blade 17, the latter of which is connected to a rotor 18. Floorgate 16 in the closed position retains pellet samples within test chamber 11 and in the open position, discharges the contents of the test chamber, e.g. pellets, pellet fragments and pellet fines, into housing 12. The opening and closing of floorgate 16 is effected by movement of lever 19 which can h=manually or automatically operated. FIG. 2 illustrates floorgate 16 in both the open and closed positions.

The size, shape and materials of construction of test chamber 11 can vary, as can the size, shape and materials of construction of blade 17, rotor 18, inlet chamber 10 and housing 12. In the embodiment of FIG. 1, test chamber 11 is a cylinder concentrically fitted within housing 12, which is also a cylinder, and attached to the top wall of housing 12. Housing 12 itself is optional and the position of the test chamber within the housing can also vary to convenience.

In the embodiment of FIG. 1, test chamber 11 is constructed of a durable screen material, the size, shape and number of holes of which can vary. Floorgate 16 is constructed of similar material, while inlet chamber 10 and housing 12 are constructed of nonporous material.

Rotor 18 is connected to an electric motor 20 which in turn is connected to a control panel 21 by cable 22 which is typically electric and typically includes signal, sensing, etc., means. For example, cable 22 usually includes or is connected to means for sensing te amperage draw of motor 20 and for communicating this information back to control panel 21. Control panel 21 can be equipped with a variety of accessories, such as a timer or clock, and it can has either fixed to or an integral part of or located totally apart from housing 12. Its ultimate location with respect to the pellet durability tester is a function of convenience.

In the operation of this particular embodiment, the pellet durability tester of FIG. 1 is situated in conjunction with a pelleting mill in such a manner that a sample of freshly milled pellets can be collected, either manually or automatically, directly into sample inlet chamber 10 through entrance port 13. The sample is held within inlet chamber 10 until it is ready to be transferred to test chamber 11. The sample is transferred by opening floorgate 15, which causes the pellets to drop into test chamber 11. Transfer is effected by gravity and while the sample is being disintegrated in chamber 11, a new sample can has collected into inlet chamber 10. The sample entry into test chamber 11 from sample inlet chamber 10 is preferably an all-at-once method of entry as opposed to a metered flow method of entry. The same method of entry is used for all samples tested.

Figure 3:
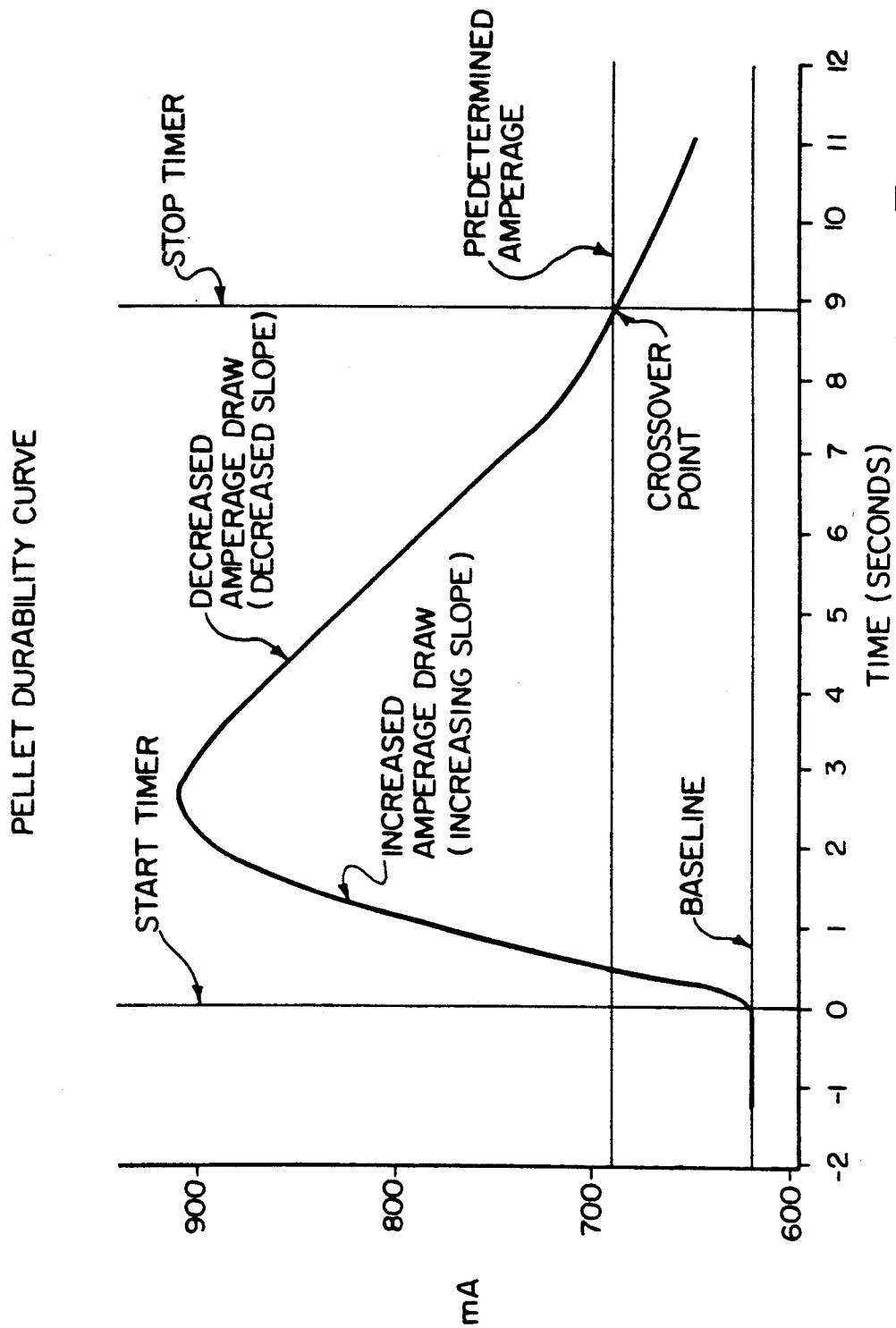
FIG. 3 is an illustrative pellet durability curve.

Reference is made to FIG. 3. Prior to entry of the sample into test chamber 11, electric motor is turning rotor 10 and blade 17 at a constant rate. This is driven by a steady, regulated supply of power to electric motor 20 and if necessary, this supply is regulated by a constant voltage transformer and/or a variable autotransformer (neither shown). Just prior to the sample entering test chamber 11, a baseline for the main drive amperage level is determined. The pellet sample is then introduced into test chamber 11 which results in an increased amperage draw (the increasing slope of the durability curve) by electric motor 20. When amperage increases above the baseline, a timer component of control panel 21 is initiated. As the sample is agitated by blade 17, the pellets will begin to disintegrate. Pellet fines and fragments will be discharged from test chamber 11 through the holes of the mesh defining its volume and as this occurs, the main drive amperage will begin to gradually decrease the decreasing slope of the durability curve). The dynamic amperage, i.e. the amperage above the baseline, is continually checked against a predetermined setpoint amperage which is greater than the baseline amperage (i.e. the line above and parallel to the baseline in FIG. 3). When the dynamic amperage equals or is less than the predetermined amperage (i.e. the crossover point on FIG. 3), the timer is terminated and the test time recorded. This crossover point can occur virtually anywhere along the decreasing slope of the durability curve, including the point at which it rejoins the baseline, but is typically chosen at or near a point along this part of the curve where the highest correlation with pellet durability is obtained (as experimentally determined). As can seen from FIG. 3, the decreasing slope is relatively gradual as compared to the increasing slope and as such, considerably more time is required for the curve to return to the baseline than to reach its apex. Information derived from the tail of the decreasing slope of the curve is usually of marginal or no value relative to pellet durability and as such, can be disregarded. Once the dynamic amperage is equal the or less than the predetermined amperage, Floorgate 16 of test chamber 11 is opened and the remaining sample is discharged by any convenient means such as gravity, or by mechanical or pneumatic assist (neither shown). Floorgate 16 is then retracted into its closed position and test chamber ready to receive its next sample of pellets.

The time (or other measure of pellet disintegration) required to reduce the dynamic amperage to the same or less than the predetermined amperage can be used without modification as a durability measure of the pellets or it can converted to an existing durability standard, such as the State Pellet Quality Test. through standard regression analysis techniques.

SPECIFIC EMBODIMENT

A pellet durability tester of substantially the same configuration as that described in FIGS. 1 and 2 was positioned next to a pellet mill such that sample batches of pellets were diverted from the mill to the tester for durability analysis. The sample inlet chamber was constructed of 12 gauge steel pipe with an internal diameter of 3". The test chamber was housed in a cylindrical, steel container of 10" diameter × 10" height dimensions and fitted with a door of 5.6" × 5.1" dimensions which gave access to the test chamber. The test chamber was a 3" internal diameter, 2½" deep steel screen basket with a steel screen floorgate, all screen size holes measuring 9/64" in diameter.

The electric motor that drove the rotor and blade was a ⅛ hp Dayton, 115 vac, 1.8 amp, 3600 rpm, counter-clockwise rotation, Model 3M292A. The rotor was a ¼" driveshaft and the blade was a ¼" diameter, 2¾ length, bar with rounded edges. A constant, continuous power supply was delivered to the motor through the use of a constant voltage transformer and a variable autotransformer. The motor was connected to a control panel equipped with microprocessor/electronic monitoring equipment that included transducers, capacitors and a processor with digital and analog IO capabilities.

After power was supplied to the tester, an unscreened sample of about 200 g of animal feed pellets was transferred from the pellet will to the sample inlet chamber by way of the inlet chamber entrance port. The weight of the sample was recorded manually but this operation can be automated simply by attaching a weight sensor to the sample inlet chamber floor (e.g. gate 15) and connecting it to the microprocessor on the control panel.

Prior to the sample entering the test chamber, a baseline main drive amperage level was automatically recorded from the electric motor. The sample was then introduced into the test chamber by an "all-at-once" method of entry. The blade was rotating within the test chamber at about 3600 rpm in an unloaded condition. Introduction of the sample resulted in a decrease of rpm requiring an additional motor amperage draw in an attempt to maintain its preload rotation. Once more than about 5 additional milliamps (background noise level) above the baseline were required, a timer was automatically initiated.

The sample within the test chamber was disintegrated by the action of the blade upon the pellets and the pellets upon themselves and against the chamber walls until the pellets were reduced to pellet fines and pellet fragments that could pass through the holes of the chamber wall and floor. As this occurred, the amperage to the main drive under load conditions (i.e. the dynamic amperage) began to gradually decrease. This dynamic amperage was continually checked against a predetermined amperage greater than the baseline amperage, a value that is a function of the nature of the pellets and the test conditions and equipment. In this example, an average of about 70 milliamps above baseline amperage was desirable. When the dynamic average equalled or was less than the predetermined amperage (i.e. below the crossover point), the timer was terminated and the total elapsed time on the timer was recorded. The floorgate of the test chamber was opened to discharge the sample remains, the floorgate was subsequently closed, and the test chamber was then ready to proceed with the analysis of the next sample.

The test time was then adjusted to a 200 g sample basis using the following equation:

$$T_2 = \frac{(200 \times T_1)}{W_t} \quad (I)$$

where
$T_2$ is the adjusted test time,
$T_1$ is the test time, and
$W_t$ is the sample weight in grams.

The adjusted test time ($T_2$) was then converted to a desired conventional quality scale, here the K-State Pellet Durability Test. The equation describing the relationship between the adjusted test time ($T_2$) and the K-State Pellet Durability Index (PDI) was $$PDI = A - B \, e^{(-C \times T_2)} \quad (II)$$

where
PDI = the Pellet Quality Index (%),
A is the quality plateau (a value determined experimentally when defining the relationship between the desired test scale and the pellet durability tester),
B is the value describing the curve (also determined experimentally when defining the relationship between the desired test scale and the pellet durability tester), and
C is the value describing the curve (also determined experimentally when defining the relationship between the desired test scale and the pellet durability tester).

This equation was derived by using nonlinear regression analysis.

Figure 4:
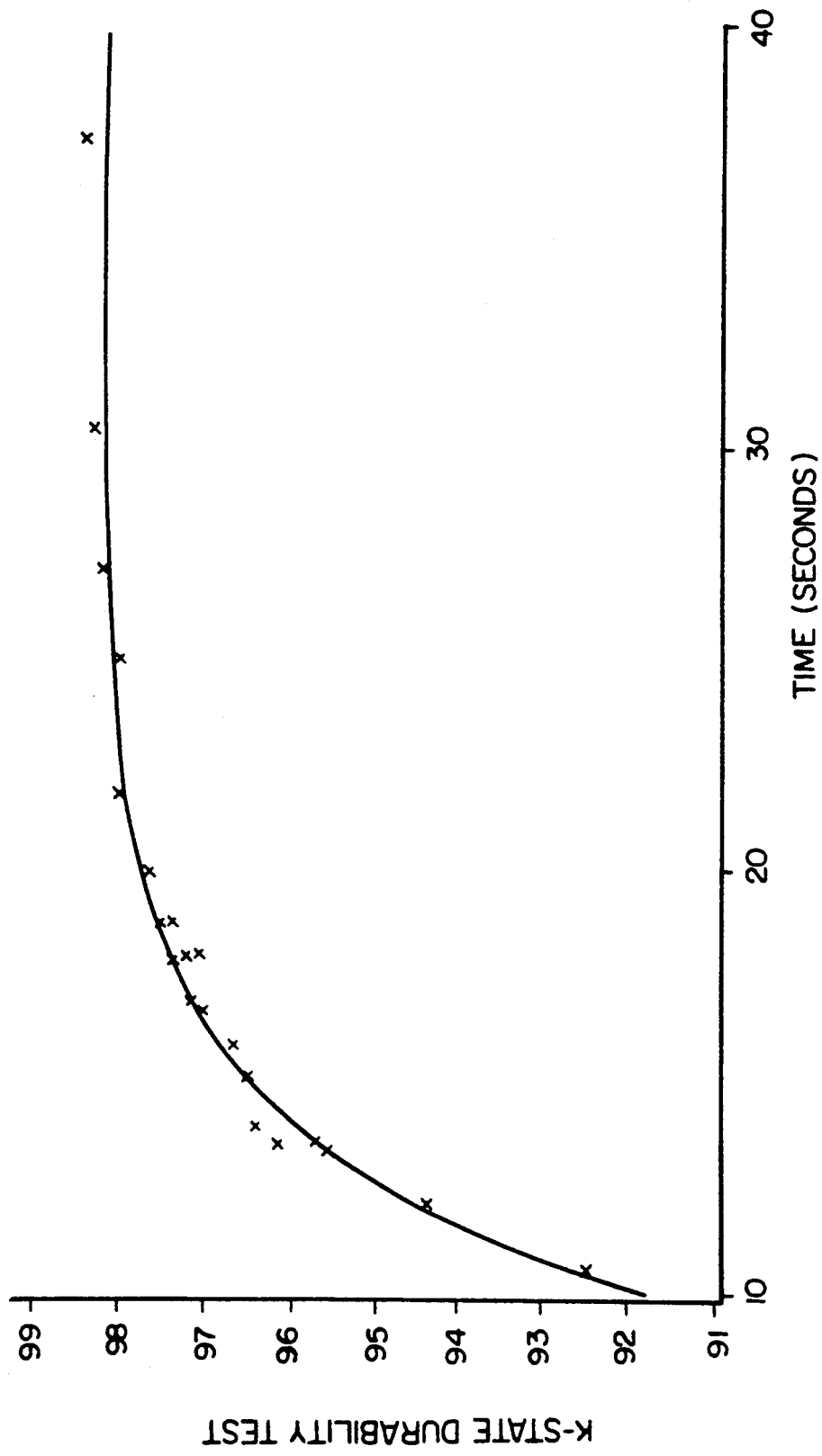
FIG. 4 is an illustrative curve showing the correlation between a durability measure of this invention (time) and the K-State Pellet Quality Test.

This procedure was used to analyze the durability of a variety of animal feed pellets. In all cases, the sample of pellets tested was divided into two batches, one batch (uncured, unscreened) tested in the pellet durability tester according to the above-described procedure, and the other batch (cured, screened) tested by the K-State Pellet Quality Test. In all cases, an excellent correlation between the two was obtained, as illustrated by the curve in FIG. 4 generated from the analysis of a sample of complete dairy feed pellets. In FIG. 4, the curve itself was generated from that one half of the pellet samples which were tested by the K-State Pellet Quality Test. The "x's" marked along the curve are various data points generated from the pellets of the other one half sample which were tested in the pellet durability tester. Typically, a pellet sample that took longer than 11 seconds to reduce the dynamic amperage to a value the same or less than that of the predetermined amperage was found to have a durability index of at least about 93.2 on the PDI.

Although this invention has been described in considerable detail through the preceding embodiment, it is to be understood that this embodiment is for the purpose of illustration only. Many variations and modifications can h=made by one skilled in the art without departing from the spirit and scope of the invention.

What is claimed is:

1. A process for measuring the durability of freshly formed, uncured pellets, the process comprising:
   A. introducing a sample of the pellets by an all-atonce method of entry into a test chamber equipped with a rotating blade for breaking the pellets into pellet fines and pellet fragments,
   B. disintegrating at least a portion of the pellets within the test chamber by breaking at least a portion of the pellets through the action of said rotating blade upon the pellets, and
   C. measuring the durability of the pellets by
      (1) measuring a power requirement to rotate the blade within the test chamber at a given rate of revolution per minute prior to the introduction of the sample of pellets,
      (2) measuring the amount of increase in the power requirement necessary to maintain the rotation of the blade at or near its rate of revolutions per minute in step (1) after the introduction of the sample of pellets into the test chamber, and
      (3) measuring the elapse of time from the first increase in power requirement required by the rotating blade after the introduction of the sample of pellets into the test chamber, to the time at which the increased power requirement has reduced to a predetermined level that is greater than or equal to the power level in step (1).

2. The process of claim 1 wherein the measured power requirement is an amperage draw on an electric motor which is attached to means for driving the rotating blade within the chamber.

3. The process of claim 2 wherein the elapse of time measured in step (3) is the measure of the durability of the sample of pellets disintegrated within the chamber.

4. The process of claim 2 wherein the elapse of time measured in step (3) is converted to an existing pellet durability index.

5. A process for measuring the durability of a sample of pellets comprising
   (a) disintegrating at least a portion of the pellets within a test chamber by contacting said pellets with a mechanical device movable within said test chamber, and
   (b) sensing the durability of the pellets by
      (1) measuring the power required to move said mechanical means in said chamber at a predetermined rate of movement prior to introduction of said pellets into said chamber,
      (2) maintaining the rate of movement of said mechanical means in said chamber at or near said predetermined rate after the introduction of said sample into said chamber by increasing the power required to move said mechanical means, and
      (3) maintaining the rate of movement of said mechanical means in said chamber at or near said predetermined rate as said pellets disintegrate by reducing the power required to move said mechanical means, and
   wherein the durability of the pellets is measured by sensing the time elapsed between increasing the power in step (2) to the time when the power in step (3) has reduced to a predetermined level.

6. The process of claim 3 wherein said mechanical device is moved in said chamber by means of an electric motor, the power required to move said mechanical device in said chamber being determined by measuring the amperage draw on said electric motor.

7. The process of claim 6 wherein said mechanical device is a rotating blade connected to said electric motor.

8. A pellet durability tester for measuring the durability of the pellets in a plurality of discrete samples of pellets comprising
   means defining a test chamber in which a samples of pellets can be disintegrated,
   feeding means for individually charging said plurality of samples into said test chamber in series, said feeding means including a gate, and being capable of regulating the intake of pellets into said test chamber,
   a mechanical device for contacting pellets in said test chamber to thereby disintegrate the pellets into pellet fragments,
   drive means attached to said mechanical device to move said mechanical device in said test chamber, and
   sensing means for sensing the power connected by said drive means.

9. The pellet durability tester of claim 8 wherein said gate is adapted to automatically charge samples into said test chamber.

10. A pellet durability tester comprising means defining a test chamber in which a sample of pellets can be disintegrated,
    a mechanical device adapted to rotate in said test chamber for contacting pellets in said test chamber to thereby disintegrate the pellets into pellet fragments,
    means to maintain the rotation of said mechanical device at or near a predetermined rate of rotation before, during and after pellet disintegration,
    an electric motor attached to said mechanical device to move said mechanical device in said test chamber,
    sensing means for sensing the amperage of the electric current used to drive said electric motor, and
    timing means for measuring the time over which said amperage increases during pellet disintegration.

11. The pellet tester of claim 10 wherein said mechanical device is a rotating blade connected to said electric motor.

12. The pellet tester of claim 10 wherein said mechanical device rotates in said chamber.

13. A pellet durability tester comprising
    means defining a test chamber in which a sample of pellets can be disintegrated,
    a mechanical device adapted to move in said test chamber for contacting pellets in said test chamber to thereby disintegrate the pellets into pellet fragments,
    means to maintaining the movement of said mechanical device at or near a predetermined rate of movement before, during and after pellet disintegration,
    drive means attached to said mechanical device for moving said mechanical device in said test chamber,
    sensing means for sensing a power requirement of said drive means, and
    timing means for measuring the time over which said power requirement increases during pellet disintegration.

14. A process for measuring the durability of a sample of pellets comprising
    (a) disintegrating at least a portion of the pellets within a test chamber by contacting said pellets with a mechanical device moveable within said test chamber, said mechanical device being attached to an electric motor for moving said mechanical device in said chamber,
    (b) directly sensing the amperage of the electric current consumed by said motor and sensing the time elapsed over the period beginning at the start of disintegration and ending when said amperage falls to a predetermined value, and
    (c) determining the durability of said pellets by comparing the time elapsed with a predetermined known relationship between said time elapsed and the durability of said pellets.

15. In a process for manufacturing cured pellets in a continuous production run in which a mixture of ingredients is formed into uncured pellets and the uncured pellets thereafter cured, the improvement comprising
    (a) periodically obtaining a sample of uncured pellets immediately after formation thereof,
    (b) measuring the durability of the pellets in each of said samples by
       (i) disintegrating at least a portion of the pellets within a test chamber by contacting said pellets with a mechanical device moveable within said test chamber, said mechanical device being attached to an electric motor for moving said mechanical device in said chamber, (ii) directly sensing the amperage of the electric current consumed by said motor and sensing the time elapsed over the period beginning at the start of disintegration and ending when said amperage falls to a predetermined value, and
(iii) determining the durability of said pellets by comparing said elapsed time with a predetermined known relationship between said elapsed time and the durability of said pellets,
(c) adjusting one or more variables in the process for forming said uncured pellets in response to the measured durability of step (b).

* * * * *